(12) United States Patent
Kannan et al.

(10) Patent No.: US 10,646,168 B2
(45) Date of Patent: *May 12, 2020

(54) DROWSINESS ONSET DETECTION

(71) Applicant: Microsoft Technology Licensing, LLC, Redmond, WA (US)

(72) Inventors: Aadharsh Kannan, Redmond, WA (US); Govind Ramaswamy, Bellevue, WA (US); Avinash Gujjar, Redmond, WA (US); Srinivas Bhaskar, Toronto (CA)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,015

(22) Filed: Mar. 23, 2018

(65) Prior Publication Data

US 2018/0214089 A1 Aug. 2, 2018

Related U.S. Application Data

(63) Continuation of application No. 14/974,584, filed on Dec. 18, 2015, now Pat. No. 9,955,925.

(51) Int. Cl.
*A61B 5/00* (2006.01)
*A61B 5/18* (2006.01)
(Continued)

(52) U.S. Cl.
CPC ........ *A61B 5/7282* (2013.01); *A61B 5/02405* (2013.01); *A61B 5/16* (2013.01);
(Continued)

(58) Field of Classification Search
CPC ..... A61B 5/7282; A61B 5/7264; A61B 5/726; A61B 5/7257
See application file for complete search history.

(56) References Cited

U.S. PATENT DOCUMENTS

| 6,822,573 B2 | 11/2004 | Basir |
| 8,519,853 B2 | 8/2013 | Eskandarian et al. |

(Continued)

FOREIGN PATENT DOCUMENTS

| CN | 101224113 A | 7/2008 |
| IN | 2950MU2015 A | 9/2015 |

OTHER PUBLICATIONS

Gupta, Nipun, "ECG and Wearable Computing for Drowsiness Detection", In Thesis of California State University, May 2014, 71 pages.

(Continued)

*Primary Examiner* — Alyssa M Alter
(74) *Attorney, Agent, or Firm* — Shook, Hardy & Bacon LLP

(57) ABSTRACT

Drowsiness onset detection implementations are presented that predict when a person transitions from a state of wakefulness to a state of drowsiness based on heart rate information. Appropriate action is then taken to stimulate the person to a state of wakefulness or notify other people of their state (with respect to drowsiness/alertness). This generally involves capturing a person's heart rate information over time using one or more heart rate (HR) sensors and then computing a heart-rate variability (HRV) signal from the captured heart rate information. The HRV signal is analyzed to extract features that are indicative of an individual's transition from a wakeful state to a drowsy state. The extracted features are input into an artificial neural net (ANN) that has been trained using the same features to identify when an individual makes the aforementioned transition to drowsiness. Whenever an onset of drowsiness is detected, a warning is initiated.

20 Claims, 7 Drawing Sheets

(51) Int. Cl.
| | |
|---|---|
| B60K 28/06 | (2006.01) |
| G08B 21/06 | (2006.01) |
| A61B 5/024 | (2006.01) |
| A61B 5/16 | (2006.01) |

(52) U.S. Cl.
CPC .............. *A61B 5/18* (2013.01); *A61B 5/6801* (2013.01); *A61B 5/726* (2013.01); *A61B 5/7257* (2013.01); *A61B 5/7264* (2013.01); *A61B 5/7267* (2013.01); *A61B 5/742* (2013.01); *A61B 5/7405* (2013.01); *A61B 5/746* (2013.01); *B60K 28/06* (2013.01); *G08B 21/06* (2013.01); *A61B 5/0024* (2013.01); *A61B 5/681* (2013.01); *A61B 5/6898* (2013.01)

(56) References Cited

U.S. PATENT DOCUMENTS

| | | | |
|---|---|---|---|
| 8,725,311 | B1 | 5/2014 | Breed |
| 9,955,925 | B2* | 5/2018 | Kannan .............. A61B 5/02405 |
| 2008/0214903 | A1 | 9/2008 | Orbach |
| 2011/0301487 | A1 | 12/2011 | Abeyratne et al. |
| 2012/0123232 | A1 | 5/2012 | Najarian et al. |
| 2012/0265080 | A1 | 10/2012 | Yu et al. |
| 2014/0378857 | A1 | 12/2014 | Masuda et al. |
| 2015/0164377 | A1 | 6/2015 | Nathan et al. |

OTHER PUBLICATIONS

Jiao, et al., "Effect of Different Vibration Frequencies on Heart Rate Variability and Driving Drowsiness in Healthy Drivers", In Proceedings of International Archives of Occupational and Environmental Health, vol. 77, issue 3, Apr. 2004, 7 pages.

Kaur, et al., "Neural Network Based Drowsiness Detection Using Electroencephalogram", In International Journal of Engineering Research & Technology, vol. 2, Issue 10, Oct. 2013, 2497-2506.

Kurta, et al., "The ANN-based Computing of Drowsy Level", In Journal of Expert Systems with Applications, vol. 36, Issue 2, Mar. 2009, 2 pages.

Lee, et al., "Mobile-based Kernel-Fuzzy-C-Means-Wavelet for Driver Fatigue Prediction with Cloud Computing", In Proceedings of IEEE Sensors, Nov. 2, 2014, 4 pages.

Lee, et al., "Wristband-Type Driver Vigilance Monitoring System Using Smartwatch", In Journal of IEEE Sensors, vol. 15, No. 10, Oct. 2015, pp. 5624-5633.

Li, et al., "Detection of Driver Drowsiness Using Wavelet Analysis of Heart Rate Variability and a Support Vector Machine Classifier", In Journal of Sensors, vol. 13, Dec. 2, 2013, pp. 16494-16511.

Liang, et al., "Changes in Physiological Parameters Induced by Indoor Simulated Driving: Effect of Lower Body Exercise at Mid-Term Break", In Proceedings of Sensors Basel, vol. 9, Issue 9, Sep. 1, 2009, pp. 6913-6933.

Malcangi, Mario, "Applying Evolutionary Methods for Early Prediction of Sleep Onset", In Journal of Neural Computing and Applications, Jun. 7, 2015, 5 pages.

Miyaji, et al., "Driver's Cognitive Distraction Detection Using Physiological Features by the Adaboost", In Proceedings of the 12th International IEEE Conference on Intelligent Transportation Systems, Oct. 3, 2009, pp. 90-95.

Murugappan, et al., Frequency Band Analysis of Electrocardiogram (ECG) Signals for Human Emotional State Classification Using Discrete Wavelet Transform (DWT), In Journal of Physical Therapy Science, vol. 25, Issue 7, Aug. 20, 2013, pp. 753-759.

Patel, et al., "Applying Neural Network Analysis on Heart Rate Variability Data to Assess Driver Fatigue", In International Journal of Expert Systems with Applications, vol. 38, Issue 6, Jun. 2011, pp. 7235-7242.

Poh, et al., "Advancements in Noncontact Multiparameter Physiological Measurements using a Webcam", In Proceedings of IEEE Transactions on Biomedical Engineering, vol. 58, Issue 1, Jan. 2011, pp. 7-11.

Ríos-Aguilar, et al., "Variation of the Heartbeat and Activity as an Indicator of Drowsiness at the Wheel Using a Smartwatch", In International Journal of Artificial Intelligence and Interactive Multimedia, vol. 3, No. 3, Jun. 2015, pp. 96-100.

Sannino, et al., "Automatic Extraction of Effective Rule Sets for Obstructive Sleep Apnea Detection for a Real-Time Mobile Monitoring System", In Proceedings of IEEE 14th International Conference on Information Reuse and Integration, Aug. 14, 2013, pp. 247-253.

Swarnkar, et al., "Objective Measure of Sleepiness and Sleep Latency via Bispectrum Analysis of EEG", In Proceedings of Medical & Biological Engineering & Computing, vol. 48, Issue 12, Dec. 2010, 8 pages.

"International Search Report and Written Opinion Issued in PCT Application No. PCT/US2016/065484", dated Mar. 6, 207, 17 Pages.

"Second Written Opinion Issued in PCT Application No. PCT/US2016/065484", dated Nov. 28, 2017, 5 Pages.

Alter Morschauser, Alyssa Margo, U.S. Office Action, U.S. Appl. No. 14/974,584, dated Oct. 19, 2017, pp. 1-14.

Alter Morschauser, Alyssa Margo, U.S. Notice of Allowance, U.S. Appl. No. 14/974,584, dated Jan. 26, 2018, pp. 1-14.

"Office Action Issued in Colombian Patent Application No. NC2018/0006480", dated Apr. 29, 2019, 17 Pages.

"International Preliminary Report on Patentability Issued in PCT Application No. PCT/US2016/065484", dated Mar. 6, 2018, 9 Pages.

"Second Office Action Issued in Colombian Patent Application No. NC2018/0006480", dated Aug. 6, 2019, 2 Pages.

"Office Action and Search Report Issued in Chilean Patent Application No. 1551-2018", dated Jul. 29, 2019, 12 Pages.

* cited by examiner

DROWSINESS ONSET DETECTION

CROSS-REFERENCE TO RELATED APPLICATIONS

This application is a continuation of U.S. application Ser. No. 14/974,584 which was filed Dec. 18, 2015.

BACKGROUND

Electroencephalography (EEG) is a method of monitoring electrical activity of the brain over time, as captured using multiple electrodes placed on the scalp. Information about a person's mental and physical condition can be derived from an analysis of the so-called brain waves observed in EEG signals. One such condition is the transition between a wakeful state and a drowsy state.

In human sleep, there are two main types of sleep—namely rapid-eye-movement (REM) sleep and non-rapid-eye-movement (NREM) sleep. REM sleep is identifiable in an EEG signal by its characteristic low-amplitude, high-frequency waves. NREM sleep is categorized in three distinct stages: N1, N2, and N3; and presents very different EEG wave patterns from REM sleep. For example, N3 NREM sleep exhibits brain waves in an EEG signal characterized by high-amplitude, low-frequency waves. In general, brain waves become slower and more synchronized as a person transitions from stage N1 to N3 sleep.

As a person falls asleep, the activity of their body slows down and their brain waves get slower and bigger. N1 NREM sleep, which is often referred to as drowsy sleep or drowsiness, usually occurs between sleep and wakefulness. This stage is characterized in EEG signals as a transition between so-called alpha waves having a frequency of 8-13 Hz (which is common in the awake state) to so-called theta waves having a frequency of 4-7 Hz. Thus, the transition from a wakeful state to a drowsy state can be easily seen in an EEG signal.

SUMMARY

The drowsiness onset detection implementations described herein generally detect the onset of drowsiness in an individual. In one general implementation this involves using one or more heart rate (HR) sensors which capture HR information of the individual, one or more computing devices and a drowsiness onset detector computer program having a plurality of sub-programs executable by the one or more computing devices. The one or more computing devices are directed by the sub-programs of the drowsiness onset detector computer program to first receive the HR information from the heart rate sensor or sensors. A set of features is then extracted from the HR information. These features, which are among many features that can be extracted from HR information, have been determined to be specifically indicative of a transition from a wakeful state of an individual to a drowsy state of an individual. Next, the extracted features are combined to produce a drowsiness detection input. The drowsiness detection input is then fed into an artificial neural network (ANN) classifier that has been trained to distinguish between the wakeful state of an individual and the drowsy state of an individual based on the extracted features. In one implementation, the ANN classifier has also been trained in part using an indicator of the transition between wakefulness and drowsiness (i.e., N1 NREM sleep) as exhibited in an EEG signal. It is next identified from an output of the ANN classifier if the drowsiness detection input indicates that the individual is exhibiting an onset of drowsiness. If so, a drowsiness onset warning is initiated.

It should be noted that the foregoing Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter. Its sole purpose is to present some concepts of the claimed subject matter in a simplified form as a prelude to the more-detailed description that is presented below.

DESCRIPTION OF THE DRAWINGS

The specific features, aspects, and advantages of the disclosure will become better understood with regard to the following description, appended claims, and accompanying drawings where:

DETAILED DESCRIPTION

Figure 1:
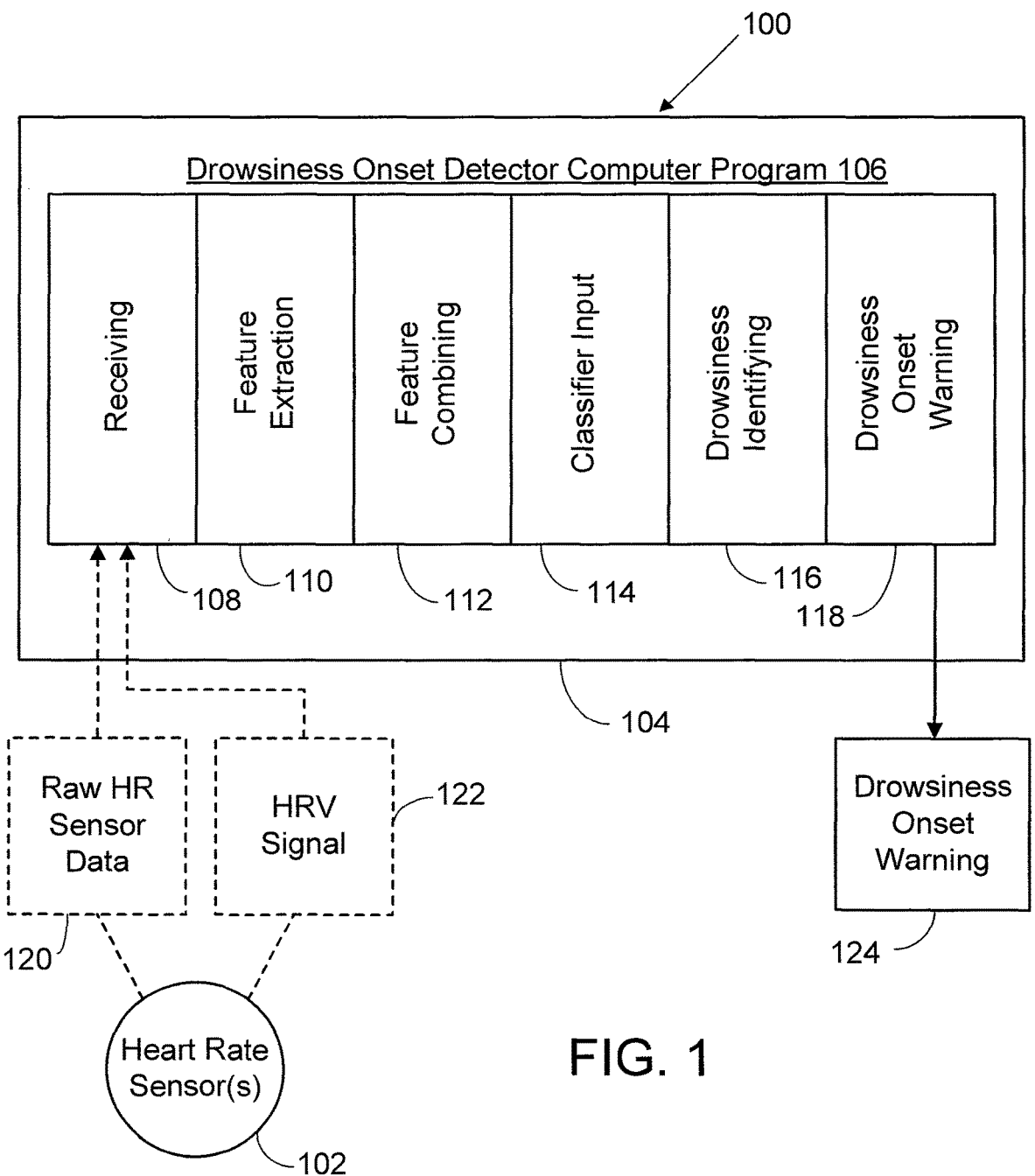
FIG. 1 is a diagram illustrating one implementation, in simplified form, of a system framework for realizing the drowsiness onset detection implementations described herein.

In the following description reference is made to the accompanying drawings which form a part hereof, and in which are shown, by way of illustration, specific versions in which drowsiness onset detection implementations can be practiced. It is understood that other implementations can be utilized and structural changes can be made without departing from the scope thereof.

It is also noted that for the sake of clarity specific terminology will be resorted to in describing the drowsiness onset detection implementations and it is not intended for these implementations to be limited to the specific terms so chosen. Furthermore, it is to be understood that each specific term includes all its technical equivalents that operate in a broadly similar manner to achieve a similar purpose. Reference herein to "one implementation", or "another implementation", or an "exemplary implementation", or an "alternate implementation" means that a particular feature, a particular structure, or particular characteristics described in connection with the implementation can be included in at least one version of the drowsiness onset detection. The appearances of the phrases "in one implementation", "in another implementation", "in an exemplary implementation", and "in an alternate implementation" in various places in the specification are not necessarily all referring to the same implementation, nor are separate or alternative implementations mutually exclusive of other implementations. Yet furthermore, the order of process flow representing one or more implementations of the project information extraction does not inherently indicate any particular order or imply any limitations thereof.

As utilized herein, the terms "component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, to the extent that the terms "includes," "including," "has," "contains," and variants thereof, and other similar words are used in either this detailed description or the claims, these terms are intended to be inclusive in a manner similar to the term "comprising" as an open transition word without precluding any additional or other elements.

1.0 Drowsiness Onset Detection

In general, the drowsiness onset detection implementations described herein can predict when a person transitions from a state of wakefulness to a state of drowsiness based on heart rate information over time. Appropriate action can then be taken to stimulate the person to a state of wakefulness or notify other people of their state (with respect to drowsiness/alertness). This is useful in many scenarios where a person's wakefulness is required, such as while driving a car, commandeering a ship, piloting an aircraft, people studying for exams, during meetings, and so on.

The drowsiness onset detection implementations described herein generally involve capturing a person's heart rate information over time using one or more heart rate (HR) sensors and then computing a heart-rate variability (HRV) signal from the captured heart rate information. This HRV signal is analyzed to extract features that are indicative of an individual's transition from a wakeful state to a drowsy state (i.e., N1 NREM sleep). The extracted features are input into an artificial neural net (ANN) that has been trained using the same features to identify when an individual makes the aforementioned transition to drowsiness. Whenever an onset of drowsiness is detected, a warning is initiated that can take various forms.

An advantageous feature of the drowsiness onset detection described herein is that the features extracted from the HRV signal have been tailored to specifically detect the transition from wakefulness to drowsiness. For example, in one implementation, just 11 features are employed as opposed to the many features that can be extracted from a HRV signal. As such, the amount of processing, as well as the time it takes to detect the onset of drowsiness, is significantly reduced.

The drowsiness onset detection implementations described herein are also advantageous for various other reasons including, but not limited to, the following. As will be appreciated from the more-detailed description that follows, some of the drowsiness onset detection implementations are self-contained. More particularly, they are either fully contained in a local HR sensor device, or employ such a device to capture HR information which is then forwarded to a computing device carried by the user. As such, outside communication is not needed (e.g., no cellular data usage), and the scheme can function even without outside connectivity (for example where cellular service is not available). In addition, the drowsiness onset detection implementations described herein are noninvasive and produce accurate results that are believed to exceed any wakefulness monitoring scheme currently being employed.

1.1 System and Process Frameworks

This section describes different exemplary implementations of a system framework and a process framework that can be used to realize the drowsiness onset detection implementations described herein. It is noted that in addition to the system framework and process framework implementations described in this section, various other system framework and process framework implementations may also be used to realize the drowsiness onset detection implementations.

FIG. 1 illustrates one implementation, in simplified form, of a system framework for realizing the drowsiness onset detection implementations described herein. As exemplified in FIG. 1, the system framework 100 includes a set of one or more heart rate (HR) sensors 102. Any type of sensor that captures the heart rate of an individual can be employed as the heart rate (HR) sensor(s) 102. In one version, these HR sensor(s) 102 are physically disposed on (e.g., worn on) the body of a user. In another version, the HR sensor(s) 102 are carried by the user 104. In yet another version, the HR sensor(s) 102 are remote from the user, but still able to detect the person's heart rate (e.g., via imaging techniques). As will be appreciated from the more detailed description that follows, the set of HR sensors 102 is configured to continuously (e.g., on an ongoing basis) and passively measure (e.g., capture) heart rate information associated with the user as they go about their day, and at least output a time-stamped data stream that includes a current value of this rate information.

Referring again to FIG. 1, the system framework 100 also includes one or more computing devices 104. In one version, a computing device 104 is resident in the HR sensor or sensors 102, thus creating a unified drowsiness onset detection device. In another version, a computing device 104 separate from the HR sensor or sensors 102 is employed. This latter version of the computing device 104 can be a mobile device that is carried by the user, such as a conventional smartphone or a conventional tablet computer. In yet another version, there is both a computing device 104 resident in the HR sensor(s) 102 and a separate computing device carried by the user. As will be described in more detail later, the computing device 104 resident in the sensor(s) 102 in this last version is used to perform at least some pre-processing of the signal(s) output by the sensor(s). For example, as will be described in more detail later, this pre-processing can involve deriving a heart rate variability (HRV) signal from the raw HR sensor readings.

As indicated above, the HR sensor or sensors 102 can take different forms. For example, in one implementation where the sensor(s) are worn on the body of a user, the HR sensor(s) 102 can be packaged in wearable device. One such wearable device is a health/fitness tracking device that is worn on an individual's wrist. It is noted that many different types of health/fitness tracking wearable computing devices are commercially available today that include HR sensors.

In the foregoing versions having a computing device 104 that is separate from the HR sensor or sensors 102, each of the HR sensors is configured to wirelessly transmit the time-stamped data stream output from the sensor(s) to the computing device. The computing device 104 is according configured to wirelessly receive the various data streams transmitted from the set of HR sensors 102. The wireless communication of the various data streams output from the set of HR sensors 102 can be realized using various wireless technologies. For example, this wireless communication can be realized using a conventional Bluetooth personal area network. Another version is possible where the wireless communication is realized using a conventional Wi-Fi local area network. Yet another version is also possible where the wireless communication is realized using a combination of different wireless networking technologies.

As exemplified in FIG. 1, the system framework 100 also includes a drowsiness onset detector computer program 106 having sub-programs executable by one or more computing devices 104. The sub-programs include a receiving sub-program 108, a feature extraction sub-program 110, a feature combining sub-program 112, an artificial neural network (ANN) classifier input sub-program 114, an onset of drowsiness identifying sub-program 116 and a drowsiness onset warning sub-program 118. In one version, raw HR sensor data 120 is input into the receiving sub-program 108 from the HR sensors 102. In another version, the aforementioned HRV signal 122 is input into the receiving sub-program 108 from the HR sensors 102. The alternate nature of these two inputs is indicated in FIG. 1 by the use of broken line arrows. A drowsiness onset warning 124 is output from the drowsiness onset warning sub-program 118. As indicated previously, each of these sub-programs is realized on the one or more computing devices (such as those described in more detail in the Exemplary Operating Environments section which follows). It is noted that whenever there is a plurality of computing devices they are in communication with each other via a computer network (such as the Internet or a proprietary intranet).

Figure 2:
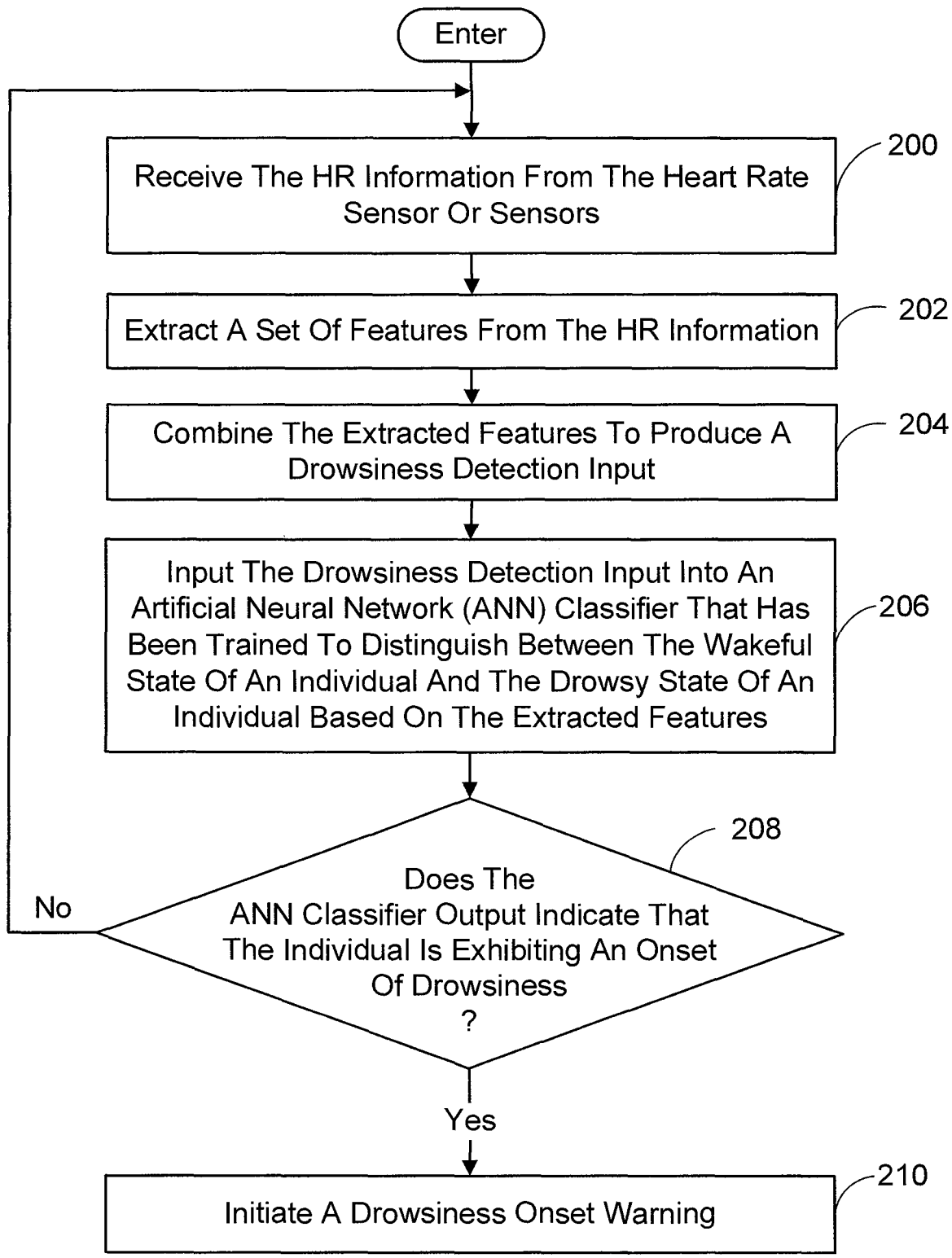
FIG. 2 is a flow diagram illustrating an exemplary implementation, in simplified form, of a process for detecting the onset of drowsiness for an individual.

Referring now to FIG. 2, the aforementioned one or more computing devices are directed by the foregoing sub-programs of the computer program to accomplish a series of process actions. More particularly, FIG. 2 illustrates an exemplary implementation, in simplified form, of a process for detecting the onset of drowsiness for an individual. This process begins with receiving the HR information from the heart rate sensor or sensors (process action 200). A set of features are then extracted from the HR information (process action 202). These features, which are among many features that can be extracted from HR information, have been determined to be specifically indicative of a transition from a wakeful state of an individual to a drowsy state of an individual. Next, the extracted features are combined to produce a drowsiness detection input (process action 204). The drowsiness detection input is input into an artificial neural network (ANN) classifier that has been trained to distinguish between the wakeful state of an individual and the drowsy state of an individual based on the extracted features (process action 206). It is then identified from an output of the ANN classifier if the drowsiness detection input indicates that the individual is exhibiting an onset of drowsiness (process action 208). If so, a drowsiness onset warning is initiated (process action 210). If not, the foregoing process is repeated.

With regard to initiating the drowsiness onset warning, the warnings can be characterized as belonging to three general categories. The first category is that of a wake-up call to the individual being monitored for drowsiness. By way of example but not limitation, the drowsiness onset warning can be a "message" that is displayed on a display screen. When the heart rate sensor or sensors are packaged such as described previously, this package can have a display. In addition, for implementations employing the aforementioned mobile device, this device can have a display. The message can be text or images, or even take the form of flashing images that appear to the user as a flashing light on the display screen. In addition to, or instead of the foregoing wake-up message examples, the wake-up message can take the form of suggestions to the individual. For example, in the context of an individual who is driving a vehicle, the message could include text providing the location of the closest hotel or rest stop. The warning can also be an audible alert (e.g., buzzing, ringing, speech, music, and so on) that is played over speaker's resident in the heart rate sensor(s) package or the mobile device. The warning can further be a haptic alert (e.g., vibration, mild electrical shock, and so on) that is created using conventional methods by the heart rate sensor(s) package or the mobile device in response to an initiating command. Any of the foregoing alerts can also be combined to create the drowsiness warning to the individual. Another type of warning involves transmitting a message to a third party (e.g., nurse, medical professional, doctor, sleep researcher, and so on) who in turn warns the individual being monitored for drowsiness, or otherwise takes action based on the individual experiencing the onset of drowsiness. Yet another type of warning is an instruction to a device to take some action in response to the individual experiencing the onset of drowsiness. For example, in the near future the individual may be driving a so-called connected car which can accept an instruction (assuming the proper security protocols are followed) to take over control of the car and drive it to a safe place (like the side of the road). Similarly, other "connected" devices could be controlled in a similar manner to avoid accidents owing to the individual's drowsiness. For example, home appliances like a stove could be turned off.

As indicated previously, the foregoing implementations and versions of drowsiness onset detection have the advantage of being self-contained. They are either fully contained in a HR sensing device, or employ such a device to capture HR information which is then forwarded to a computing device carried by the user. However, while being self-contained has its advantages, other considerations may outweigh them. For example, in a cloud based scenario, additional historical features such as a person's sleep history, current weather and other realtime info can be included. Since processing power on the cloud is typically quite large, one can conceive a more complex model that involves crunching the sleep info of multiple people at the same time. To this end, some implementations of drowsiness onset detection involve using the foregoing system elements to communicate with a server or cloud service. In this case, the raw HR sensor information or a pre-processed HRV signal is sent to the server or cloud service which would in turn detect when the onset of drowsiness occurs and issue the appropriate warning. This could involve sending a warning indicator back to the user's device(s) which would implement the warning, or to a third party, or both.

Figure 3:
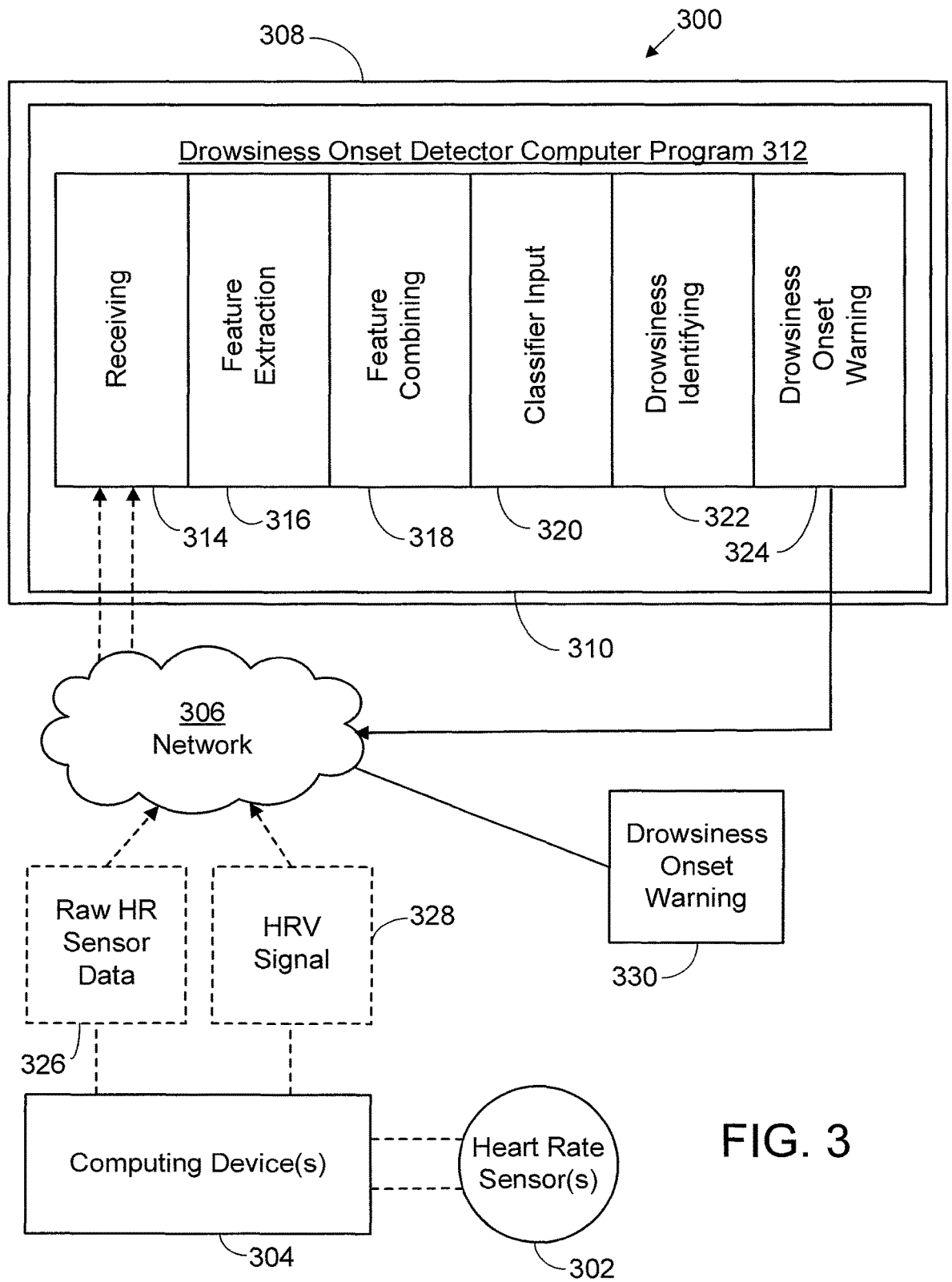
FIG. 3 is a diagram illustrating another implementation, in simplified form, of a system framework for realizing the drowsiness onset detection implementations described herein, which involves a remote server or cloud service.

FIG. 3 illustrates the foregoing alternate implementation. As exemplified in FIG. 3, the system framework 300 includes a set of one or more heart rate (HR) sensors 302. As in the previous implementations, in one version, these HR sensor(s) 302 are physically disposed on (e.g., worn on) the body of a user. In another version, the HR sensor(s) 302 are carried by the user. In yet another version, the HR sensor(s) 302 are remote from the user, but still able to detect the person's heart rate. The set of HR sensors 302 is configured to continuously (e.g., on an ongoing basis) and passively measure (e.g., capture) heart rate information associated with the user as they go about their day, and at least output a time-stamped data stream that includes a current value of this rate information. The system framework 300 also includes one or more computing devices 304. As with previous implementations, in one version, a computing device 304 is resident in the HR sensor or sensors 302. In another version, a computing device 304 separate from the HR sensor or sensors 302 is employed. This latter version of the computing device 304 can be a mobile device that is carried by the user, such as a conventional smartphone or a conventional tablet computer. In yet another version, there is both a computing device 304 resident in the HR sensor(s) 302 and a separate computing device carried by the user. As will be described in more detail later, the computing device 304 resident in the sensor(s) 302 in this last version is used to perform at least some pre-processing of the signal(s) output by the sensor(s), such as deriving the aforementioned HRV from the raw HR sensor readings. Additionally, as before, in the foregoing versions having a computing device 304 that is separate from the HR sensor or sensors 302, each of the HR sensors is configured to wirelessly transmit the time-stamped data stream output from the sensor(s) to the computing device. The computing device 304 is according configured to wirelessly receive the various data streams transmitted from the set of HR sensors 302. The wireless communication of the various data streams output from the set of HR sensors 302 can be realized using various wireless technologies. For example, this wireless communication can be realized using a conventional Bluetooth personal area network. Another version is possible where the wireless communication is realized using a conventional Wi-Fi local area network. Yet another version is also possible where the wireless communication is realized using a combination of different wireless networking technologies.

Additionally, in the implementations illustrated in FIG. 3, the computing device 304 (whether resident only in the HR sensor(s) 302 or in the form of a separated device carried by the user) is further configured to communicate over a data communication network 306 such as the Internet (among other types of networks) to a cloud service 308 that operates on one or more other computing devices 310 that are remotely located from the computing device 304. The remote computing devices 310 can also communicate with each other via the network 306. The term "cloud service" is used herein to refer to a web application that operates in the cloud and can be hosted on (e.g., deployed at) a plurality of data centers that can be located in different geographic regions (e.g., different regions of the world). It is noted that in one version of the foregoing scheme the cloud service is replaced by a conventional remote server (not shown).

As further exemplified in FIG. 3, the system framework 300 includes a drowsiness onset detector computer program 312 operating on the one or more computing devices 310 associated with the cloud service 308 (or remote server). The drowsiness onset detector computer program 312 has sub-programs executable by the one or more computing devices 310. The sub-programs include a receiving sub-program 314, a feature extraction sub-program 316, a feature combining sub-program 318, an artificial neural network (ANN) classifier input sub-program 320, an onset of drowsiness identifying sub-program 322 and a drowsiness onset warning sub-program 324. In one version, raw HR sensor data 326 is received from the computing device 304 is input into the receiving sub-program 314. In another version, the aforementioned HRV signal 328 is input into the receiving sub-program 314. The alternate nature of these two inputs is indicated in FIG. 3 by the use of broken line arrows. A drowsiness onset warning 330 is output via the network 306 from drowsiness onset warning sub-program 324. As indicated previously, each of these sub-programs is realized on the one or more computing devices (such as those described in more detail in the Exemplary Operating Environments section which follows). It is noted that whenever there is a plurality of computing devices they are in communication with each other via a computer network (such as the Internet or a proprietary intranet).

Figure 4:
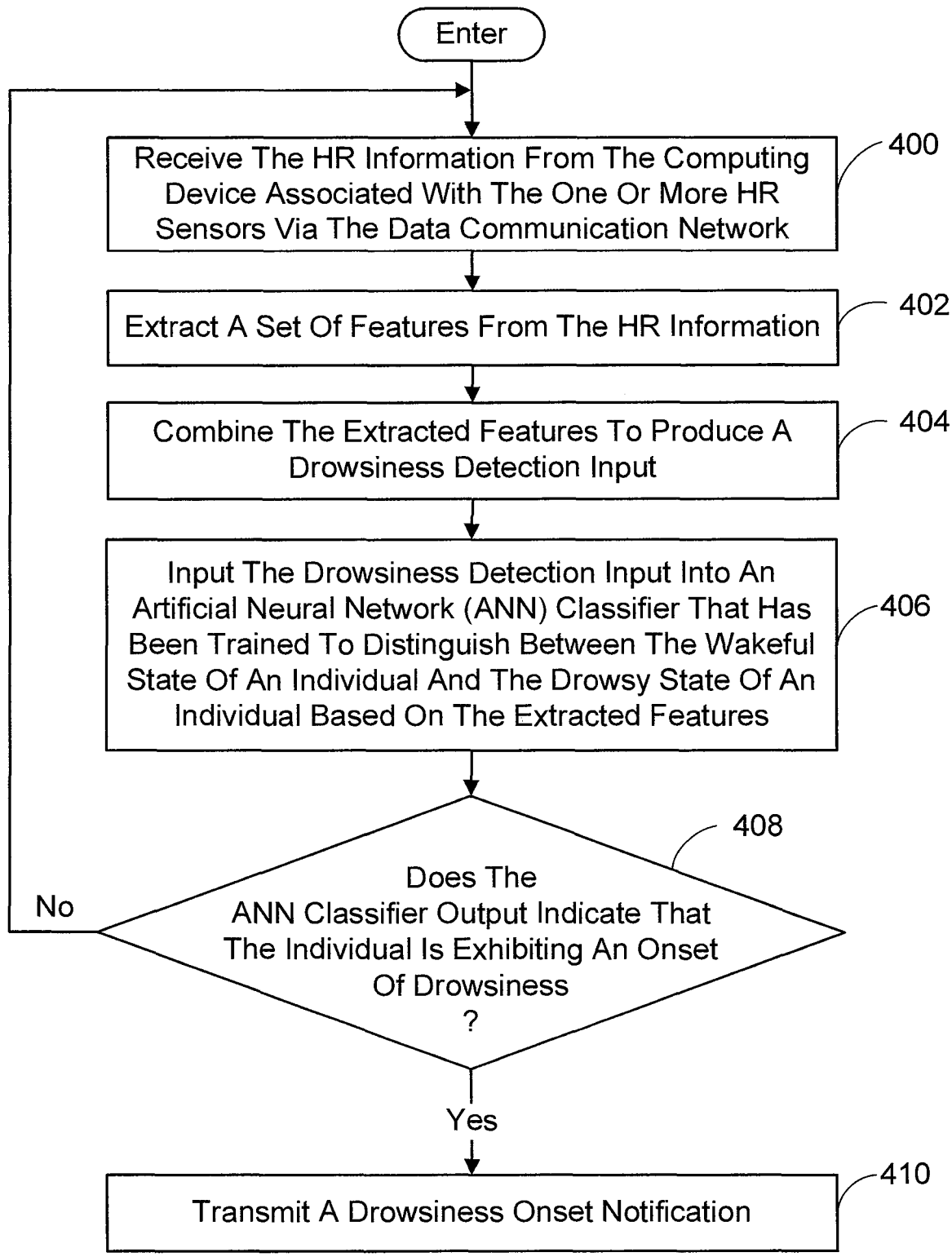
FIG. 4 is a flow diagram illustrating an exemplary implementation, in simplified form, of a process for detecting the onset of drowsiness for an individual, which involves a remote server or cloud service.

Referring now to FIG. 4, the aforementioned one or more computing devices associated with the cloud service (or remote server) are directed by the foregoing sub-programs of the drowsiness onset detector computer program to accomplish a series of process actions. More particularly, FIG. 4 illustrates an exemplary implementation, in simplified form, of a process for detecting the onset of drowsiness for an individual. The process begins with receiving HR information of the individual (process action 400). This HR information is received from the computing device associated with the aforementioned one or more HR sensors via the data communication network. A set of features are then extracted from the HR information (process action 402). These features, which are among many features that can be extracted from HR information, have been determined to be specifically indicative of a transition from a wakeful state of an individual to a drowsy state of an individual. Next, the extracted features are combined to produce a drowsiness detection input (process action 404). The drowsiness detection input is input into an artificial neural network (ANN) classifier that has been trained to distinguish between the wakeful state of an individual and the drowsy state of an individual based on the extracted features (process action 406). It is then identified from an output of the ANN classifier if the drowsiness detection input indicates that the individual is exhibiting an onset of drowsiness (process action 408). If so, a drowsiness onset notification is transmitted (process action 410). If not, the foregoing process is repeated.

As described previously, the self-contained implementations (such as illustrated in FIGS. 1 and 2) initiate a drowsiness onset warning. The drowsiness onset notification transmitted by the cloud service (or remote server) is used for a similar effect. As indicated previously one of type of warning involves a wake-up call to the individual being monitored for drowsiness. Namely, by way of example but not limitation, the drowsiness onset notification can be a "message" that is transmitted to the previously described packaged heart rate sensor or sensors or the aforementioned mobile device. This message can be text or images that are displayed on a display screen associated with the sensor(s) or mobile device, or even take the form of flashing images that appear to the user as a flashing light on the display. In addition to, or instead of the foregoing wake-up message examples, the wake-up message can take the form of suggestions to the individual. For example, in the context of an individual who is driving a vehicle, the message could include text providing the location of the closest hotel or rest stop. The message can also take the form of an instruction to create an audible alert (e.g., buzzing, ringing, speech, music, and so on) that is played over speakers resident in the sensor(s) or mobile device. The message can further take the form of an instruction to create a haptic alert (e.g., vibration, mild electrical shock, and so on) that is created using conventional methods by the sensor(s) or mobile device. As before, any of the foregoing alerts can be combined to create the drowsiness warning to the individual. Another type of notification involves transmitting a message to a third party (e.g., nurse, medical professional, doctor, sleep researcher, and so on) who in turn warns the individual being monitored for drowsiness, or otherwise takes action based on the individual experiencing the onset of drowsiness. Yet another type of notification that the cloud service (or server) could transmit is an instruction to a device to take some action in response to the individual experiencing the onset of drowsiness. For example, in the near future the individual may be driving a so-called connected car which can accept an instruction (assuming the proper security protocols are followed) to take over control of the car and drive it to a safe place (like the side of the road). Similarly, other "connected" devices could be controlled in a similar manner to avoid accidents owing to the individual's drowsiness. For example, home appliances like a stove could be turned off.

1.2 Feature Extraction

As indicted previously, in either the self-contained or cloud service-based implementations, an artificial neural network (ANN) classifier that has been trained to distinguish between the wakeful state of an individual and the drowsy state of an individual based on the aforementioned extracted features is employed to detect the onset of drowsiness in an individual being monitored. In this section, exemplary feature extraction methods and exemplary types of features that are extracted will be described.

Medical research indicates that heart rate and an individual's perception of drowsiness are connected. More particularly, it is possible to detect when an individual transition from a wakeful state to a drowsy state (i.e., N1 NREM sleep) using a measure of that person's heart rate. The wave pattern produced by a typical electrocardiogram (EKG or ECG) includes a series of QRS wave complexes. Each of these complexes is made up of a combination of three deflections—namely the deflections referred to as the Q-wave, R-wave and S-wave. The Q-wave and S-wave are typically characterized by an initial negative or downward deflection, while the R-wave is typically characterized by an initial positive or upward deflection. The time elapsed between two consecutive R waves in the electrocardiogram is referred to as an RR interval. The HR sensor or sensors employed in drowsiness onset detection implementations described herein are capable of at least detecting the R-wave peaks. In one implementation, the detected R-wave peaks forms the aforementioned raw HR signal captured by the HR sensor or sensors. Heart rate variability (HRV) is the physiological phenomenon of variation in the time interval between the R-wave peaks. It is measured by the variation in the RR interval. The HRV signal is computed from the raw HR signal either by a computing device associated with the HR sensor(s), or a separate computing device (such as a mobile device carried by the individual being monitored, or by computing device(s) associated with a cloud service (or remote server)).

In one implementation, as the HRV signal is generated, it is segmented into a sequence of prescribed-length segments. In one version, these segments are two minutes in length and represent approximately 120 RR interval values (i.e., a 1 Hz signal segment). In one implementation, the two minute segments of the HRV signal are then up-sampled prior to feature extraction. More particularly, curve fitting techniques (such cubic spline interpolation) are employed to model the variation seen in the RR interval values of the segment as an equation. The resulting equations are then sampled. In one version, where 120 RR intervals are represented by the equations, 840 samples are taken using conventional methods. This represents a seven fold up-sampling of the original HRV segment. This up-sampling (i.e., 1 Hz to 7 Hz) is performed as it was found a 7 Hz signal segment operates well with the feature extraction methods to be described shortly.

In one implementation, the aforementioned prescribed-length HRV signal segments are taken from the HRV signal on a rolling window basis such that there is a prescribed offset time between each segment. For example, in the case of a two minute long segment, the offset can being any time period greater than 0 and less than 2 minutes. In one version, a 1 minute offset is employed such that 50% of the data is common with the previous segment and 50% is new data.

The aforementioned set of features is extracted from each consecutive segment of the up-sampled HRV signal. In one implementation, this feature extraction generally involves the use of a Discrete Fast Fourier Transform (DFFT), and a Discrete Wavelet Transform (DWT) employing a set of Symlet mother waves of order 3. While many characteristics can be derived from the resulting frequency transformed HRV signal segment, it has been found that the ratio of the power of the low frequency (LF) components to the power of the high frequency (HF) components is particularly indicative of the transition between wakefulness and drowsiness. As such, in one implementation, this LF to HF power ratio is chosen as one of the aforementioned extracted features.

With regard to the DWT, in one implementation, an 8-level decomposition of the HRV segment is performed. The entropy of a difference between the decomposed segment and the Symlet mother waves at each level is computed using conventional methods to produce a series of upper range D entropy coefficients (i.e., $D_1, \ldots, D_8$) and a series of lower range A entropy coefficients (i.e., $A_1, \ldots, A_8$). Various averages of the coefficients can also be computed and employed as extracted features, among other combinations. However, it has been found that some of the DWT coefficients and combinations are more indicative of the transition between wakefulness and drowsiness, than others. For example, it has been found that the following DWT coefficients are more indicative of the transition than the others:

a) $D_1$ through $D_8$ entropy coefficients;
b) $A_8$ entropy coefficient; and
c) the mean of the $A_1$ through $A_8$ entropy coefficients Accordingly, of the many coefficients that can be extracted using DFFT and DWT analyses of the HRV segments, the eleven coefficients described above (i.e., LF/HF power ratio, $D_1$ through $D_8$ entropy, $A_8$ entropy, and $A_1$ through $A_8$ entropy mean) were found to provide a specific indication of the transition between wakefulness and drowsiness.

1.3 Classifier Training

Figure 5:
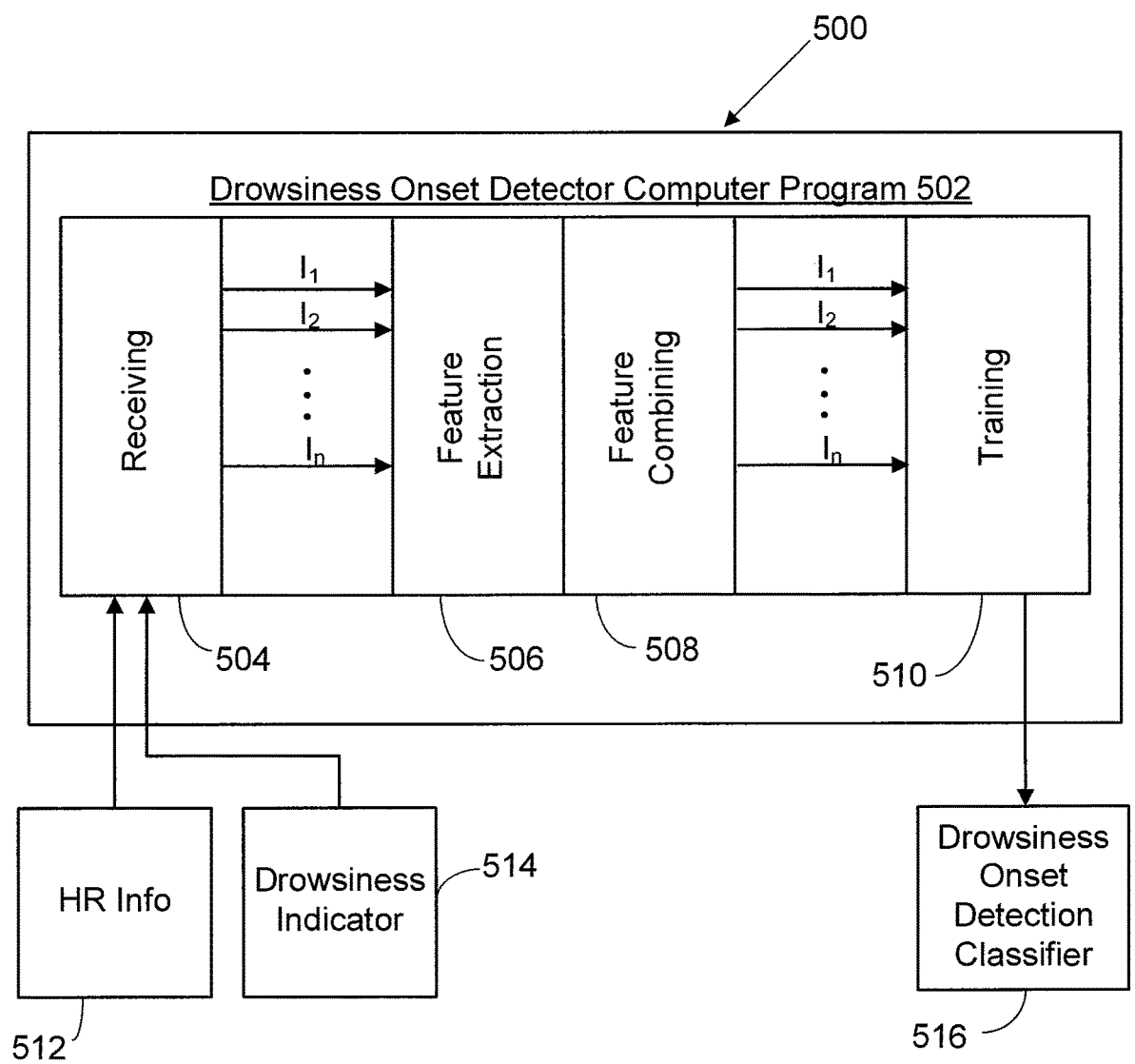
FIG. 5 is a diagram illustrating an exemplary implementation, in simplified form, of a system framework for training a drowsiness onset detection classifier, which in turn can be used to detect the onset of drowsiness in an individual.

FIG. 5 illustrates an exemplary implementation, in simplified form, of a system framework used in training a drowsiness onset detection classifier which in turn can be used to detect the onset of drowsiness in an individual. As exemplified in FIG. 5, the system framework 500 includes a drowsiness onset detector training computer program 502 having sub-programs executable by one or more computing devices. These sub-programs include a receiving sub-program 504, and for the HR information associated with each of a plurality of individuals ($I_1, I_2, \ldots, I_n$), an extracting sub-program 506 and a combining sub-program 508. In addition, there is a training sub-program 510 that is trained using the output of the combining sub-program for each individual ($I_1, I_2, \ldots, I_n$). HR information 512 output by one or more heart rate sensors for a plurality of individuals, as well as a drowsiness indicator 514 for each of the individuals specifying whether that individual is in a wakeful state or in a drowsy state, are input to the receiving sub-program 504. A trained drowsiness onset detection classifier 516 is output from the training sub-program 510. Each of these sub-programs is realized on one or more computing devices such as that described in more detail in the Exemplary Operating Environments section which follows. It is noted that whenever there is a plurality of computing devices they can be in communication with each other via a computer network (such as the Internet or a proprietary intranet).

Figure 6:
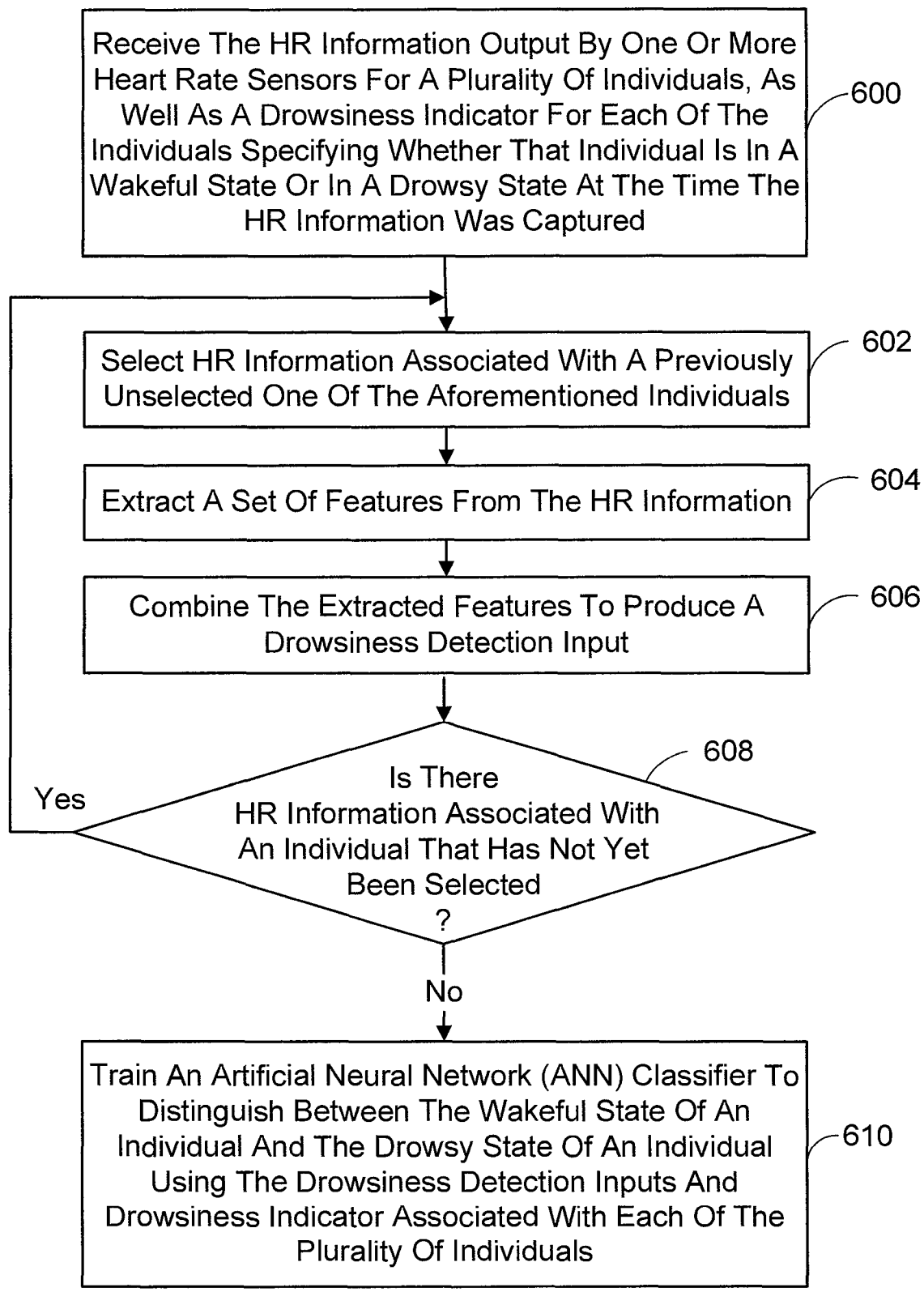
FIG. 6 is a flow diagram illustrating an exemplary implementation, in simplified form, of a process for training a drowsiness onset detection classifier.

Referring now to FIG. 6, the aforementioned one or more computing devices are directed by the foregoing sub-programs of the drowsiness onset detector training computer program to accomplish a series of process actions. More particularly, HR information output by one or more heart rate sensors for a plurality of individuals, as well as a drowsiness indicator for each of the individuals specifying whether that individual is in a wakeful state or in a drowsy state at the time the HR information was captured, are received via the receiving sub-program (process action 600). In one implementation, the drowsiness indicator is derived from an EEG signal captured using the previously-described electroencephalography methods for identifying whether a person is in a wakeful state of a drowsy state (i.e., N1 NREM sleep). Further, the HR information captured and the associated drowsiness indicator correspond to times the individual was transitioning from a wakeful state to a drowsy state.

HR information associated with a previously unselected one of the aforementioned individuals is selected next (process action 602). A set of features is extracted from the selected HR information using the extracting sub-program (process action 604). These features, which are among many features that can be extracted from HR information, have been determined to be specifically indicative of a transition from a wakeful state of an individual to a drowsy state of an individual. The extracted features are then combined to produce a drowsiness detection input using the combining sub-program (process action 606). It is next determined if there is HR information associated with an individual that has not yet been selected and processed (process action 608). If there is, then process actions 602 through 608 are repeated. When the HR information associated with all the individuals has been selected and processed, the training sub-program then trains an artificial neural network (ANN) classifier to distinguish between the wakeful state of an individual and the drowsy state of an individual using the drowsiness detection inputs and drowsiness indicator associated with each of the plurality of individuals. (process action 610). This training is accomplished using conventional ANN training methods.

2.0 Exemplary Operating Environments

Figure 7:
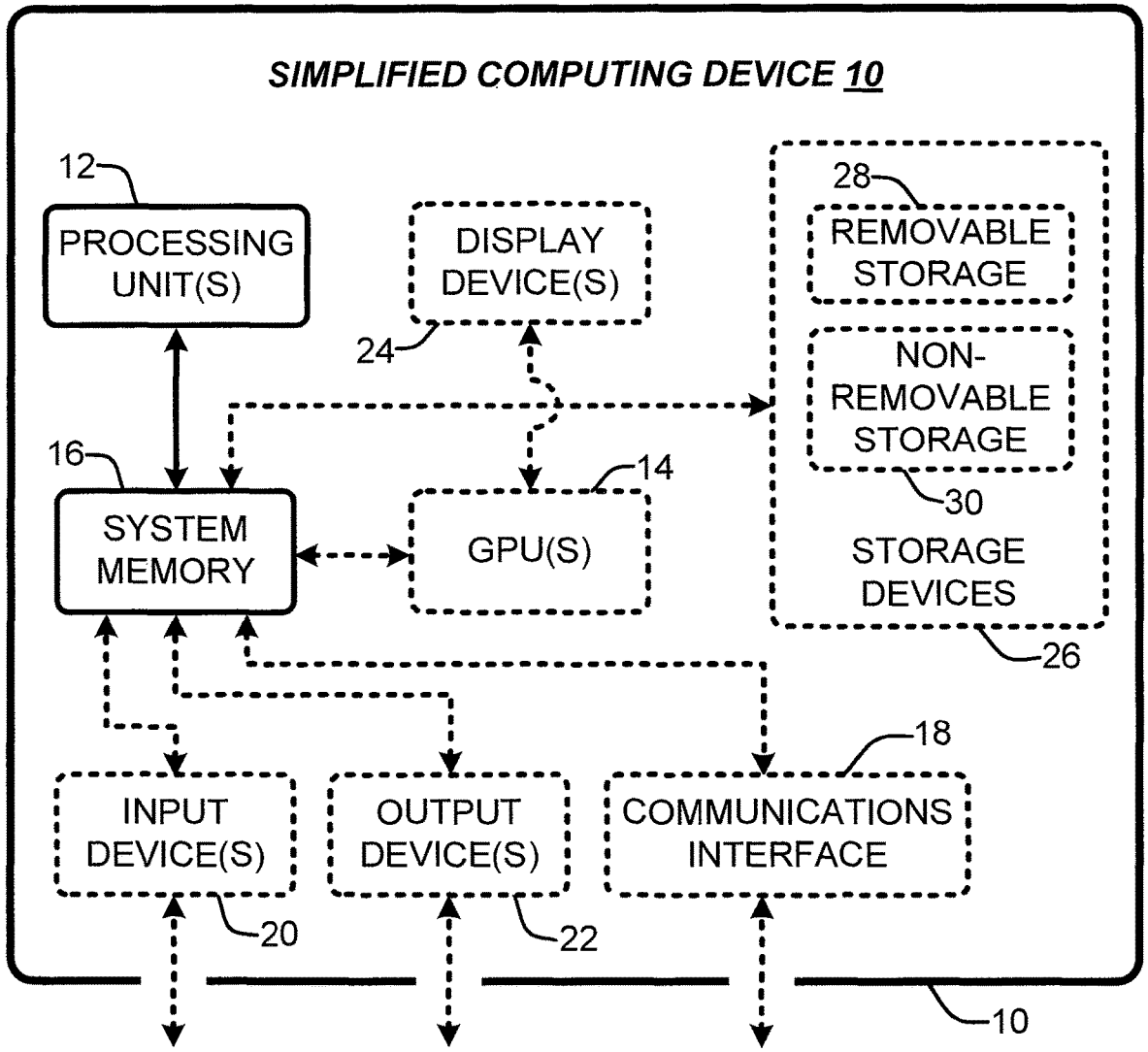
FIG. 7 is a diagram depicting a general purpose computing device constituting an exemplary system for use with the drowsiness onset detection implementations described herein.

The drowsiness onset detection implementations described herein are operational using numerous types of general purpose or special purpose computing system environments or configurations. FIG. 7 illustrates a simplified example of a general-purpose computer system with which various aspects and elements of drowsiness onset detection, as described herein, may be implemented. It is noted that any boxes that are represented by broken or dashed lines in the simplified computing device 10 shown in FIG. 7 represent alternate implementations of the simplified computing device. As described below, any or all of these alternate implementations may be used in combination with other alternate implementations that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To realize the drowsiness onset detection implementations described herein, the device should have a sufficient computational capability and system memory to enable basic computational operations. In particular, the computational capability of the simplified computing device 10 shown in FIG. 7 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 may also include other components, such as, for example, a communications interface 18. The simplified computing device 10 may also include one or more conventional computer input devices 20 (e.g., touchscreens, touch-sensitive surfaces, pointing devices, keyboards, audio input devices, voice or speech-based input and control devices, video input devices, haptic input devices, devices for receiving wired or wireless data transmissions, and the like) or any combination of such devices.

Similarly, various interactions with the simplified computing device 10 and with any other component or feature of wearable sensing, including input, output, control, feedback, and response to one or more users or other devices or systems associated with drowsiness onset detection, are enabled by a variety of Natural User Interface (NUI) scenarios. The NUI techniques and scenarios include, but are not limited to, interface technologies that allow one or more users user to interact in a "natural" manner, free from artificial constraints imposed by input devices such as mice, keyboards, remote controls, and the like.

Such NUI implementations are enabled by the use of various techniques including, but not limited to, using NUI information derived from user speech or vocalizations captured via microphones or other sensors. Such NUI implementations are also enabled by the use of various techniques including, but not limited to, information derived from a user's facial expressions and from the positions, motions, or orientations of a user's hands, fingers, wrists, arms, legs, body, head, eyes, and the like, where such information may be captured using various types of 2D or depth imaging devices such as stereoscopic or time-of-flight camera systems, infrared camera systems, RGB (red, green and blue) camera systems, and the like, or any combination of such devices. Further examples of such NUI implementations include, but are not limited to, NUI information derived from touch and stylus recognition, gesture recognition (both onscreen and adjacent to the screen or display surface), air or contact-based gestures, user touch (on various surfaces, objects or other users), hover-based inputs or actions, and the like. Such NUI implementations may also include, but are not limited, the use of various predictive machine intelligence processes that evaluate current or past user behaviors, inputs, actions, etc., either alone or in combination with other NUI information, to predict information such as user intentions, desires, and/or goals. Regardless of the type or source of the NUI-based information, such information may then be used to initiate, terminate, or otherwise control or interact with one or more inputs, outputs, actions, or functional features of the drowsiness onset detection implementations described herein.

However, it should be understood that the aforementioned exemplary NUI scenarios may be further augmented by combining the use of artificial constraints or additional signals with any combination of NUI inputs. Such artificial constraints or additional signals may be imposed or generated by input devices such as mice, keyboards, and remote controls, or by a variety of remote or user worn devices such as accelerometers, electromyography (EMG) sensors for receiving myoelectric signals representative of electrical signals generated by user's muscles, heart-rate monitors, galvanic skin conduction sensors for measuring user perspiration, wearable or remote biosensors for measuring or otherwise sensing user brain activity or electric fields, wearable or remote biosensors for measuring user body temperature changes or differentials, and the like. Any such information derived from these types of artificial constraints or additional signals may be combined with any one or more NUI inputs to initiate, terminate, or otherwise control or interact with one or more inputs, outputs, actions, or functional features of the drowsiness onset detection implementations described herein.

The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 7 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, programs, sub-programs, or other data. Computer-readable media includes computer storage media and communication media. Computer storage media refers to tangible computer-readable or machine-readable media or storage devices such as digital versatile disks (DVDs), blu-ray discs (BD), compact discs (CDs), floppy disks, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and key drive), magnetic cassettes, magnetic tapes, magnetic disk storage, magnetic strips, or other magnetic storage devices. Further, a propagated signal is not included within the scope of computer-readable storage media.

Retention of information such as computer-readable or computer-executable instructions, data structures, programs, sub-program, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various drowsiness onset detection implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The drowsiness onset detection implementations described herein may be further described in the general context of computer-executable instructions, such as programs, being executed by a computing device. Generally, programs include routines, programs, objects, components, data structures, and the like, that perform particular tasks or implement particular abstract data types. The drowsiness onset detection implementations described herein may also be practiced in distributed computing environments where tasks are performed by one or more remote processing devices, or within a cloud of one or more devices, that are linked through one or more communications networks. In a distributed computing environment, programs may be located in both local and remote computer storage media including media storage devices. Additionally, the aforementioned instructions may be implemented, in part or in whole, as hardware logic circuits, which may or may not include a processor.

Alternatively, or in addition, the functionality described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), and so on.

3.0 Other Implementations

It is noted that any or all of the aforementioned implementations throughout the description may be used in any combination desired to form additional hybrid implementations. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What has been described above includes example implementations. It is, of course, not possible to describe every conceivable combination of components or methodologies for purposes of describing the claimed subject matter, but one of ordinary skill in the art may recognize that many further combinations and permutations are possible. Accordingly, the claimed subject matter is intended to embrace all such alterations, modifications, and variations that fall within the spirit and scope of the appended claims.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the foregoing implementations include a system as well as a computer-readable storage media having computer-executable instructions for performing the acts and/or events of the various methods of the claimed subject matter.

There are multiple ways of realizing the foregoing implementations (such as an appropriate application programming interface (API), tool kit, driver code, operating system, control, standalone or downloadable software object, or the like), which enable applications and services to use the implementations described herein. The claimed subject matter contemplates this use from the standpoint of an API (or other software object), as well as from the standpoint of a software or hardware object that operates according to the implementations set forth herein. Thus, various implementations described herein may have aspects that are wholly in hardware, or partly in hardware and partly in software, or wholly in software.

The aforementioned systems have been described with respect to interaction between several components. It will be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (e.g., hierarchical components).

Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

4.0 Claim Support And Further Implementations

The following paragraphs summarize various examples of implementations which may be claimed in the present document. However, it should be understood that the implementations summarized below are not intended to limit the subject matter which may be claimed in view of the foregoing descriptions. Further, any or all of the implementations summarized below may be claimed in any desired combination with some or all of the implementations described throughout the foregoing description and any implementations illustrated in one or more of the figures, and any other implementations described below. In addition, it should be noted that the following implementations are intended to be understood in view of the foregoing description and figures described throughout this document.

In one implementation, a system is employed for detecting the onset of drowsiness in an individual. This system includes one or more heart rate (HR) sensors which capture HR information of the individual, and one or more computing devices, the computing devices being in communication with each other via a computer network whenever there is a plurality of computing devices. The system also includes a drowsiness onset detector computer program having a plurality of sub-programs executable by the one or more computing devices. The one or more computing devices are directed by the sub-programs of the drowsiness onset detector computer program to receive the HR information from the heart rate sensor or sensors, extract a set of features from the HR information (which are among many features that can be extracted from HR information) that have been determined to be specifically indicative of a transition from a wakeful state of an individual to a drowsy state of an individual, combine the extracted features to produce a drowsiness detection input, input the drowsiness detection input into an artificial neural network (ANN) classifier that has been trained to distinguish between the wakeful state of an individual and the drowsy state of an individual based on the extracted features, identify from an output of the ANN classifier if the drowsiness detection input indicates that the individual is exhibiting an onset of drowsiness, and whenever the drowsiness detection input indicates that the individual is exhibiting an onset of drowsiness, initiate a drowsiness onset warning.

In one implementation of the system where the HR information includes a raw HR signal captured by the one or more HR sensors, the sub-program for extracting the set of features from the HR information includes first computing a heart rate variability (HRV) signal from the raw HR signal. In another implementation of the system, the one or more HR sensors includes a computing device which computes a heart rate variability (HRV) signal from a raw HR signal captured by the HR sensor or sensors. The aforementioned HR information includes this HRV signal. In yet another implementation, the one or more heart rate (HR) sensors and the one or more computing devices are resident in a unified drowsiness onset detection device. In one version of this implementation, the drowsiness onset detection device is either a wearable device worn on the person of the individual, or a mobile device carried by the individual. In still another implementation, the one or more heart rate (HR) sensors are resident in a wearable device worn on the person of the individual, and the one or more computing devices are resident in a mobile device carried by the individual, and the wearable device is in wireless communication with the mobile device. In one version of this implementation, the HR information includes a raw HR signal captured by the one or more HR sensors which is transmitted to the mobile device carried by the individual. In another version, the HR information includes a raw HR signal captured by the one or more HR sensors, and the one or more HR sensors includes a computing device which computes a heart rate variability (HRV) signal from the raw HR signal, where the HRV signal is transmitted to the mobile device carried by the individual.

One implementation of the system further includes a segmenting sub-program that is executed before the execution of the sub-program for extracting the set of features from the HR information. This segmenting sub-program segments the HR information received from the heart rate sensor or sensors into a sequence of prescribed-length segments whenever the received HR information is in the form of a heart rate variability (HRV) signal. In addition, the segmenting sub-program computes a HRV signal from the received HR information whenever the received HR information is not in the form of a heart rate variability (HRV) signal before segmenting the HRV signal into the sequence of prescribed-length segments. The sub-programs for extracting a set of features from the HR information, combining the extracted features, inputting the drowsiness detection input into the ANN classifier, identifying from an output of the ANN classifier if the drowsiness detection input indicates that the individual is exhibiting an onset of drowsiness, and whenever the drowsiness detection input indicates that the individual is exhibiting an onset of drowsiness, initiating a drowsiness onset warning, are executed on each of the HRV signal segments as they are created. In one version, thses prescribed-length segments of the HRV signal are each two minutes in length and represent a rolling window such that there is a prescribed offset time between each segment. In one variant, each two minute long HRV signal segment represents approximately 120 heart rate variation values, and the segmenting sub-program further includes up-sampling each HRV signal segment to approximately 840 samples heart rate variation values using curve fitting techniques. In another version, the sub-program for extracting the set of features from each HRV signal segment includes extracting the set of features using a Discrete Fast Fourier Transform (DFFT) and a Discrete Wavelet Transform (DWT). In one variant, the DFFT is used to compute a ratio of the power of the low frequency components of the HRV signal segment to the power of the high frequency (HF) components of the HRV signal segment as an extracted feature, and the DWT is used to compute from an 8-level decomposition of the HRV segment the $D_1$ through $D_8$ entropy coefficients, $A_8$ entropy coefficient and the mean of the $A_1$ through $A_8$ entropy coefficients as extracted features.

In one implementation of the system, the sub-program for initiating a drowsiness onset warning includes initiating a wake-up call to the individual in the form of a message that is displayed on a display screen that is viewable by the individual. In one version, this message includes text, or images, or flashing images that appear as a flashing light on the display screen, or any combination of of the foregoing. In another implementation, the sub-program for initiating a drowsiness onset warning includes initiating a wake-up call to the individual in the form of an audible alert that is played over speakers which are within a hearing range of the individual. In yet another implementation, the sub-program for initiating a drowsiness onset warning includes initiating a wake-up call to the individual in the form of a haptic alert that can be felt by the individual. In still another implementation, the sub-program for initiating a drowsiness onset warning includes transmitting a message to a third party that requests the third party to warn the individual.

In one implementation, another system is employed for detecting the onset of drowsiness in an individual. This system includes one or more computing devices, the computing devices being in communication with each other via a computer network whenever there is a plurality of computing devices. The system also includes a drowsiness onset detector computer program having a plurality of sub-programs executable by the one or more computing devices. The one or more computing devices are directed by the sub-programs of the drowsiness onset detector computer program to receive heart rate (HR) information of the individual, where the one or more computing devices are in communication over a data communication network with a remote computing device associated with one or more HR sensors which capture the HR information, and where the HR information is received from the remote computing device via the data communication network. The one or more computing devices are also directed by the sub-programs of the drowsiness onset detector computer program to extract a set of features from the HR information (which are among many features that can be extracted from HR information) that have been determined to be specifically indicative of a transition from a wakeful state of an individual to a drowsy state of an individual, combine the extracted features to produce a drowsiness detection input, input the drowsiness detection input into an artificial neural network (ANN) classifier that has been trained to distinguish between the wakeful state of an individual and the drowsy state of an individual based on the extracted features, identify from an output of the ANN classifier if the drowsiness detection input indicates that the individual is exhibiting an onset of drowsiness, and whenever the drowsiness detection input indicates that the individual is exhibiting an onset of drowsiness, transmit a drowsiness onset notification.

In one implementation, another system is employed for training a drowsiness onset detection classifier. This system includes one or more computing devices, the computing devices being in communication with each other via a computer network whenever there is a plurality of computing devices. The system also includes a drowsiness onset detector training computer program having a plurality of sub-programs executable by the one or more computing devices. The one or more computing devices are directed by the sub-programs of the drowsiness onset detector training computer program to receive the HR information output by one or more heart rate sensors for a plurality of individuals, as well as a drowsiness indicator for each of the individuals specifying whether that individual is in a wakeful state or in a drowsy state at the time the HR information was captured. For the HR information associated with each of the plurality of individuals, a set of features is extracted from the HR information (which are among many features that can be extracted from HR information) that have been determined to be specifically indicative of a transition from a wakeful state of an individual to a drowsy state of an individual, and the extracted features are combined to produce a drowsiness detection input. An artificial neural network (ANN) classifier is trained to distinguish between the wakeful state of an individual and the drowsy state of an individual using the the drowsiness detection inputs and drowsiness indicator associated with each of the plurality of individuals.

In one implementation, a computer-implemented process is employed for detecting the onset of drowsiness in an individual, which includes using a computing device to perform the following process actions: receiving the HR information from the heart rate sensor or sensors, extracting a set of features from the HR information (which are among many features that can be extracted from HR information) that have been determined to be specifically indicative of a transition from a wakeful state of an individual to a drowsy state of an individual, combining the extracted features to produce a drowsiness detection input, inputting the drowsiness detection input into an artificial neural network (ANN) classifier that has been trained to distinguish between the wakeful state of an individual and the drowsy state of an individual based on the extracted features, identifying from an output of the ANN classifier if the drowsiness detection input indicates that the individual is exhibiting an onset of drowsiness, and whenever the drowsiness detection input indicates that the individual is exhibiting an onset of drowsiness, initiating a drowsiness onset warning.

In another implementation, a computer-implemented process is employed for detecting the onset of drowsiness in an individual, which includes using a computing device to perform the following process actions: receiving heart rate (HR) information of the individual, where one or more computing devices are in communication over a data communication network with a remote computing device associated with one or more HR sensors which capture the HR information, and where the HR information is received from the remote computing device via the data communication network. Process actions are also included for extracting a set of features from the HR information (which are among many features that can be extracted from HR information) that have been determined to be specifically indicative of a transition from a wakeful state of an individual to a drowsy state of an individual, combining the extracted features to produce a drowsiness detection input, inputting the drowsiness detection input into an artificial neural network (ANN) classifier that has been trained to distinguish between the wakeful state of an individual and the drowsy state of an individual based on the extracted features, identifying from an output of the ANN classifier if the drowsiness detection input indicates that the individual is exhibiting an onset of drowsiness, and whenever the drowsiness detection input indicates that the individual is exhibiting an onset of drowsiness, transmitting a drowsiness onset notification.

In another implementation, a computer-implemented process is employed for training a drowsiness onset detection classifier, which includes using a computing device to perform the following process actions: receiving the HR information output by one or more heart rate sensors for a plurality of individuals, as well as a drowsiness indicator for each of the individuals specifying whether that individual is in a wakeful state or in a drowsy state at the time the HR information was captured. For the HR information associated with each of the plurality of individuals, extracting a set of features from the HR information (which are among many features that can be extracted from HR information) that have been determined to be specifically indicative of a transition from a wakeful state of an individual to a drowsy state of an individual, and combining the extracted features to produce a drowsiness detection input. An artificial neural network (ANN) classifier is then trained to distinguish between the wakeful state of an individual and the drowsy state of an individual using the drowsiness detection inputs and drowsiness indicator associated with each of the plurality of individuals.

In one implementation, detecting the onset of drowsiness in an individual includes using a computing device to perform the following process steps: a receiving step for receiving the HR information from the heart rate sensor or sensors, an extracting step for extracting a set of features from the HR information (which are among many features that can be extracted from HR information) that have been determined to be specifically indicative of a transition from a wakeful state of an individual to a drowsy state of an individual, a combining step for combining the extracted features to produce a drowsiness detection input, an inputting step for inputting the drowsiness detection input into an artificial neural network (ANN) classifier that has been trained to distinguish between the wakeful state of an individual and the drowsy state of an individual based on the extracted features, an identifying step for identifying from an output of the ANN classifier if the drowsiness detection input indicates that the individual is exhibiting an onset of drowsiness, and whenever the drowsiness detection input indicates that the individual is exhibiting an onset of drowsiness, performing an initiating step for initiating a drowsiness onset warning.

In another one implementation, detecting the onset of drowsiness in an individual includes using a computing device to perform the following process steps: a receiving step for receiving heart rate (HR) information of the individual, where one or more computing devices are in communication over a data communication network with a remote computing device associated with one or more HR sensors which capture the HR information, and where the HR information is received from the remote computing device via the data communication network. The process steps further include an extracting step for extracting a set of features from the HR information (which are among many features that can be extracted from HR information) that have been determined to be specifically indicative of a transition from a wakeful state of an individual to a drowsy state of an individual, a combining step for combining the extracted features to produce a drowsiness detection input, an inputting step for inputting the drowsiness detection input into an artificial neural network (ANN) classifier that has been trained to distinguish between the wakeful state of an individual and the drowsy state of an individual based on the extracted features, an identifying step for identifying from an output of the ANN classifier if the drowsiness detection input indicates that the individual is exhibiting an onset of drowsiness, and whenever the drowsiness detection input indicates that the individual is exhibiting an onset of drowsiness, performing a transmitting step for transmitting a drowsiness onset notification.

In another one implementation, training a drowsiness onset detection classifier includes using a computing device to perform the following process steps: a receiving step for receiving the HR information output by one or more heart rate sensors for a plurality of individuals, as well as a drowsiness indicator for each of the individuals specifying whether that individual is in a wakeful state or in a drowsy state at the time the HR information was captured. For the HR information associated with each of the plurality of individuals, performing an extracting step for extracting a set of features from the HR information (which are among many features that can be extracted from HR information) that have been determined to be specifically indicative of a transition from a wakeful state of an individual to a drowsy state of an individual, and a combining step for combining the extracted features to produce a drowsiness detection input. A training step is then performed for training an artificial neural network (ANN) classifier to distinguish between the wakeful state of an individual and the drowsy state of an individual using the drowsiness detection inputs and drowsiness indicator associated with each of the plurality of individuals.

Wherefore, what is claimed is:
1. A method for detecting the onset of drowsiness in an individual, comprising:

receiving heart rate (HR) information associated with the individual over time, the HR information including heart rate variability (HRV) information;

extracting a plurality of different HRV-related features from the HR information, the extracted different HRV-related features indicative of the individual transitioning from a wakeful state to a drowsy state;

combining the extracted different HRV-related features to produce a drowsiness detection input;

inputting, into an artificial neural network (ANN) classifier trained to distinguish between wakeful states of an individual and drowsy states of an individual, the drowsiness detection input to distinguish between the wakeful state and the drowsy state of the individual;

determining, based at least on the distinguishing, whether the individual is exhibiting an onset of drowsiness; and based at least on determining that the individual is exhibiting an onset of drowsiness, initiating a drowsiness onset warning.

2. A computer-readable storage medium having computer-executable instructions stored thereon that, based on execution by at least one processing system associated with at least one computing device, configure the at least one processing system to:

receive heart rate (HR) information associated with an individual over time, the HR information including heart rate variability (HRV) information;

extract a plurality of different HRV-related features from the HR information, the extracted different HRV-related features indicative of the individual transitioning from a wakeful state to a drowsy state;

combine the extracted different HRV-related features to produce a drowsiness detection input;

inputting, into an artificial neural network (ANN) classifier trained to distinguish between wakeful states of an individual and drowsy states of an individual, the drowsiness detection input to distinguish between the wakeful state and the drowsy state of the individual;

determine, based at least on the distinguishing, whether the individual is exhibiting an onset of drowsiness; and based at least on determining that the individual is exhibiting an onset of drowsiness, initiate a drowsiness onset warning.

3. A computing system for detecting the onset of drowsiness in an individual, comprising:

one or more heart rate (HR) sensors configured to capture HR information of the individual over time, the HR information including heart rate variability (HRV) information; and computer-executable instructions that, based on execution by at least one processing system associated with the computing system, configure the at least one processing system to:

receive the HR information from the one or more HR sensors;

extract a plurality of different HRV-related features from the HR information, the extracted different HRV-related features indicative of the individual transitioning from a wakeful state to a drowsy state;

combine the extracted different HRV-related features to produce a drowsiness detection input;

inputting, into an artificial neural network (ANN) classifier trained to distinguish between wakeful states of an individual and drowsy states of an individual, the drowsiness detection input to distinguish between the wakeful state and the drowsy state of the individual based;

determine, based at least on the distinguishing, whether the individual is exhibiting an onset of drowsiness; and based at least on determining that the individual is exhibiting an onset of drowsiness, initiate a drowsiness onset warning.

4. The computing system of claim 3, wherein the HR information comprises a raw HR signal captured by the one or more HR sensors, and wherein the instruction for extracting the plurality of different HRV features from the HR information, comprises first computing a HRV signal from the raw HR signal.

5. The computing system of claim 3, wherein the one or more HR sensors comprises a computing device which computes a HRV signal from a raw HR signal captured by the HR sensor or sensors, and wherein the HR information comprises the HRV signal.

6. The computing system of claim 3, wherein the one or more HR sensors and the at least one processing system are resident in a unified drowsiness onset detection device.

7. The computing system of claim 6, wherein the drowsiness onset detection device is either a wearable device worn on the person of said individual, or a mobile device carried by said individual.

8. The computing system of claim 3, wherein the one or more HR sensors are resident in a wearable device worn on the person of said individual, and the at least one processing system are resident in a mobile device carried by said individual, and wherein the wearable device is in wireless communication with the mobile device.

9. The computing system of claim 8, wherein the HR information comprises a raw HR signal captured by the one or more HR sensors which is transmitted to said mobile device carried by the individual.

10. The computing system of claim 8, wherein the HR information comprises a raw HR signal captured by the one or more HR sensors, and wherein the one or more HR sensors comprises a computing device which computes a HRV signal from the raw HR signal, said HRV signal being transmitted to said mobile device carried by the individual.

11. The computing system of claim 3, further comprising a segmenting instruction that is executed before the execution of the instruction for extracting the plurality of different HRV-related features from the HR information, said segmenting instruction segmenting the HR information received from the one or more HR sensors into a sequence of prescribed-length segments whenever the received HR information is in the form of a HRV signal, and said segmenting instruction computing a HRV signal from the received HR information whenever the received HR information is not in the form of a HRV signal before segmenting the HRV signal into the sequence of prescribed-length segments, and wherein the instructions for extracting the plurality of different HRV-related features from the HR information, combining the extracted different HRV-related features, if the individual is exhibiting an onset of drowsiness, and based at least on determining that the individual is exhibiting an onset of drowsiness, initiating the drowsiness onset warning, are executed on each of the HRV signal segments as they are created.

12. The computing system of claim 11, wherein the prescribed-length segments of the HRV signal are each two minutes in length and represent a rolling window such that there is a prescribed offset time between each segment.

13. The computing system of claim 12, wherein each two minute long HRV signal segment represents approximately 120 heart rate variation values, and wherein the segmenting instruction further comprises up-sampling each HRV signal segment to approximately 840 samples heart rate variation values using curve fitting techniques.

14. The computing system of claim 11, wherein the instruction for extracting the plurality of different HRV-related features from each HRV signal segment comprises extracting the plurality of different HRV-related features using a Discrete Fast Fourier Transform (DFFT) and a Discrete Wavelet Transform (DWT).

15. The computing system of claim 14, wherein the DFFT is used to compute a ratio of the power of the low frequency components of the HRV signal segment to the power of the high frequency (HF) components of the HRV signal segment as an extracted feature, and wherein the DWT is used to compute from an 8-level decomposition of the HRV segment the $D_1$ through $D_8$ entropy coefficients, $A_8$ entropy coefficient and the mean of the $A_1$ through $A_8$ entropy coefficients as extracted features.

16. The computing system of claim 3, wherein the instruction for initiating the drowsiness onset warning, comprises initiating a wake-up call to the individual in the form of a message that is displayed on a display screen that is viewable by the individual.

17. The computing system of claim 16, wherein the message comprises at least one of text, or images, or flashing images that appear as a flashing light on the display screen.

18. The computing system of claim 3, wherein the instruction for initiating the drowsiness onset warning, comprises initiating a wake-up call to the individual in the form of an audible alert that is played over speakers which are within a hearing range of the individual.

19. The computing system of claim 3, wherein the instruction for initiating the drowsiness onset warning, comprises initiating a wake-up call to the individual in the form of a haptic alert that can be felt by the individual.

20. The computing system of claim 3, wherein the instruction for initiating the drowsiness onset warning, comprises transmitting a message to a third party requesting the third party to warn the individual.

\* \* \* \* \*